United States Patent
Chase

(10) Patent No.: US 9,962,112 B2
(45) Date of Patent: May 8, 2018

(54) MEDICAL SYSTEMS AND METHODS OF USE

(75) Inventor: H. Peter Chase, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 402 days.

(21) Appl. No.: 12/373,888

(22) PCT Filed: Jul. 16, 2007

(86) PCT No.: PCT/US2007/073633
§ 371 (c)(1),
(2), (4) Date: Jan. 14, 2009

(87) PCT Pub. No.: WO2008/011389
PCT Pub. Date: Jan. 24, 2008

(65) Prior Publication Data
US 2010/0056993 A1    Mar. 4, 2010

Related U.S. Application Data

(60) Provisional application No. 60/807,991, filed on Jul. 21, 2006.

(51) Int. Cl.
*A61M 31/00* (2006.01)
*A61B 5/145* (2006.01)
*A61M 5/142* (2006.01)
*A61M 5/172* (2006.01)

(52) U.S. Cl.
CPC ..... *A61B 5/14532* (2013.01); *A61M 5/14244* (2013.01); *A61M 5/14276* (2013.01); *A61M 5/1723* (2013.01); *A61M 2005/14208* (2013.01); *A61M 2205/3523* (2013.01)

(58) Field of Classification Search
CPC .............. A61B 5/14532; A61B 5/1495; A61B 5/14546; A61B 5/0002; A61M 2005/14208; A61M 2205/3523; A61M 5/14244; A61M 5/14276; A61M 5/1723; A61M 2230/005; A61M 2230/201; C12Q 1/006
USPC .......................................................... 604/66
See application file for complete search history.

(56) References Cited

U.S. PATENT DOCUMENTS

| | | | |
|---|---|---|---|
| 6,873,268 B2* | 3/2005 | Lebel et al. ............. | 340/870.16 |
| 2004/0220517 A1* | 11/2004 | Starkweather ........ | A61M 5/172 |
| | | | 604/67 |
| 2005/0171503 A1* | 8/2005 | Van Den Berghe et al. . | 604/504 |
| 2008/0051764 A1* | 2/2008 | Dent ...................... | A61K 38/28 |
| | | | 604/890.1 |
| 2008/0058625 A1* | 3/2008 | McGarraugh et al. ....... | 600/347 |

* cited by examiner

*Primary Examiner* — Jason Flick
(74) *Attorney, Agent, or Firm* — Michael M. McGaw; Smith & Hopen, P.A.

(57) ABSTRACT

This invention provides ambulatory medical systems that include a monitoring device, a therapeutic substance administering device, and a receiver-controller for receiving a signal generated by the monitoring device and controlling the therapeutic substance administering device based on the information received from the monitoring device. The invention also provides methods for using the same.

20 Claims, No Drawings

MEDICAL SYSTEMS AND METHODS OF USE

CROSS-REFERENCE TO RELATED APPLICATIONS

This application claims the priority benefit of U.S. Provisional Application No. 60/807,991, filed Jul. 21, 2006, which is incorporated herein by reference in its entirety.

FIELD OF THE INVENTION

This invention relates to medical systems and methods of use. In particular, the medical systems include a monitoring device, a therapeutic substance administering device, and a receiver-controller for receiving a signal generated by the monitoring device and controlling the therapeutic substance administering device based on the information received from the monitoring device.

BACKGROUND OF THE INVENTION

Currently, therapeutic substance delivery or administering devices (e.g., implantable infusion pumps for dispensing a therapeutic substance, such as the MMT2001 Implantable Pump System sold by Minimed Inc., of Northridge, Calif. for insulin infusion) are commercially available. In addition, real-time continuous monitoring of a selected state of a body are also available, e.g., glucose monitoring devices, such as the MiniMed Guardian™, the MiniMed Continuous Glucose Monitoring System™ (CGMS), and the DexCOm™ STS™.

Currently no device is commercially available that can communicate both with the monitoring device and the therapeutic substance delivery device to control the delivery of the therapeutic substance based on the selected state of the subject's body. Such a device will allow automated monitoring of a subject's condition and provide appropriate delivery of therapeutic agents when needed. This automated system will be useful in avoiding or reducing a potentially dangerous situation from occurring.

Therefore, there is a need for a receiver-controller type device that can receive a signal generated by the monitoring device and control the operation of the therapeutic substance delivery device based on the signal it receives from the monitoring device.

SUMMARY OF THE INVENTION

One aspect of the invention provides a medical system comprising:
  a monitoring device comprising an electronic control circuitry that is configured to monitor a selected state of the body, wherein said monitoring device further comprises a telemetry system;
  a therapeutic substance delivery device comprising an electronic control circuitry that is configured to deliver a therapeutic substance to a patient; and
  a receiver-controller device comprising an electronic circuitry that is configured to receive a signal generated by said monitoring device and is further configured to control the operation of said therapeutic substance delivery device based on the signal generated by said monitoring device.

In one particular embodiment, the monitoring device monitors the glucose level of the patient. In some instances, the monitoring device measures blood glucose level. In other instances, the monitoring device measures subcutaneous glucose level.

In another embodiment, the therapeutic substance delivery device is configured to deliver insulin to the patient. Within this embodiment, in some instances the receiver-controller is configured to stop delivery of insulin under a warning condition. In other instances, the receiver-controller is configured to start delivery of insulin under a warning condition.

In some embodiments, the receiver-controller can be programmed for various warning conditions. In one example, the warning condition as measured by the monitoring device is selected from the following glucose concentration conditions in a subject: (a) the glucose level is 130-150 mg/dl and the glucose level decreases at a rate of 2 mg/dl-min or higher; (b) the glucose level is from about 100 mg/dl to about 130 mg/dl and the glucose level decreases at a rate of from about 1 to about 2 mg/dl-min or higher; and (c) the glucose level is 70 mg/dl or lower. While the above levels are one particular illustration of warning conditions, the invention is not limited to these particular conditions as the levels may vary depending on the individual.

Still in other embodiments, the medical system further comprises an alarm system for providing a signal to the patient during the warning condition. The alarm signal can be of any of the known sensory eliciting alarm system, such as tactile (e.g., touch), smell, visual, and audible. In some embodiments, the signal is audible, visible, tactile, or a combination thereof.

Yet in other embodiments, the telemetry system comprises a wireless transmitter for transmitting a signal to the receiver-controller device. Wireless transmission of data are well known to one skilled in the art of electronic communication and includes, but are not limited to, radio wave transmission, such as the Bluetooth technology. In other instances, the telemetry system can transmit its signal (e.g., measurement or reading of a selected state of the body) through a wire.

Another aspect of the invention provides a method for monitoring and/or treating diabetes in a patient. The method generally comprises:
  monitoring the glucose level in a patient with a monitoring device comprising an electronic control circuitry that is configured to monitor the glucose level in the patient, wherein the monitoring device further comprises a telemetry system; and
  ceasing or reducing insulin administration to the patient when the glucose level in the patient falls within a warning condition using a therapeutic substance delivery device comprising an electronic control circuitry that is configured to control the administration of insulin to a patient,
wherein the operation of the therapeutic substance delivery device is controlled by a receiver-controller device comprising an electronic circuitry that is configured to receive a signal generated by the monitoring device and is further configured to control the therapeutic substance delivery device based on the signal generated by the monitoring device.

The method of the invention can further comprise providing a warning signal to the patient when a potentially dangerous conditions arise. For example, when (a) the glucose level measured by the monitor is at about 130 mg/dl or lower and the rate of glucose level decrease as measured by the monitor is about 2 mg/dl-min or higher; (b) the glucose level measured by the monitor is from about 100 mg/dl to about 130 mg/dl and the rate of glucose level decrease as measured by the monitor is 1 mg/dl-min or higher; or (c) the glucose level measured by the monitor is about 70 mg/dl or less. The alarm signal can be of any of the known sensory eliciting alarm system, such as tactile (e.g., touch), smell, visual, and audible. In some embodiments, the warning signal is audible, visible, tactile, or a combination thereof.

In some embodiments, the step of monitoring glucose level comprises measuring subcutaneous glucose level of the patient.

Yet in other embodiments, the step of monitoring glucose level comprises measuring blood glucose level of the patient.

Yet another aspect of the invention provides a method for administering insulin to a subject comprising:
- monitoring the glucose level in a patient with a monitoring device comprising an electronic control circuitry that is configured to monitor the glucose level in the patient, wherein the monitoring device further comprises a telemetry system; and
- delivering insulin to the patient when the glucose level in the patient falls within a warning condition using a therapeutic substance delivery device comprising an electronic control circuitry that is configured to control administration of insulin to a patient, wherein the operation of the therapeutic substance delivery device is controlled by a receiver-controller device comprising an electronic circuitry that is configured to receive a signal generated by the monitoring device and is further configured to control the therapeutic substance delivery device based on the signal generated by the monitoring device.

DETAILED DESCRIPTION OF THE INVENTION

While the devices and methods of the invention can be used in monitoring a wide variety of body conditions, e.g., diabetes, inflammation, pain, etc., the invention will now be described with regard to monitoring and/or treating diabetic conditions, e.g., monitoring the glucose level and delivering insulin, to assist in illustrating various features of the invention. In this regard, the present invention generally relates to medical system and methods for using the same for monitoring a selected state of the body (e.g., glucose level) and delivering a therapeutic substance (e.g., insulin) to a patient.

In this regard, one aspect of the invention provides a medical system comprising:
- a monitoring device comprising an electronic control circuitry that is configured to monitor a selected state of the body, where the monitoring device further comprises a telemetry system;
- a therapeutic substance delivery device comprising an electronic control circuitry that is configured to deliver a therapeutic substance to a patient; and
- a receiver-controller device comprising an electronic circuitry that is configured to receive a signal generated by the monitoring device and is further configured to control the operation of the therapeutic substance delivery device based on the signal it receives from the monitoring device.

A therapeutic substance refers to any substance that can modulate the selected state of the body. Exemplary therapeutic substances include, but are not limited to, drugs, hormones (e.g., insulin, glucagon, amylin, and derivatives), other proteins (e.g., enzymes), electromagnetic radiation, and any other substances that can modulate the selected state of the body.

For monitoring and/or treating diabetes, the monitoring device monitors the glucose level of the patient. In some instances, the monitoring device provides real-time continuous monitoring of the glucose level. There are a number of real-time continuous glucose monitoring devices are available, such as the MiniMed Guardian™, the MiniMed Continuous Glucose Monitoring System™ (CGMS), and the DexCOm™ STS™. While the majority of real-time glucose monitoring devices measure the subcutaneous glucose level, it should be appreciated that the invention is not limited to measuring the subcutaneous glucose level. The invention also includes devices that can measure the blood glucose level. Moreover, monitoring the glucose level need not be continuous. For example, a monitoring device that measures the glucose level at a given time interval can also be used, e.g., once every few minutes such as every 30, 20, 10, 5, or 1 minutes.

The glucose level can be measured subcutaneously or by blood analysis. It should be noted that, without being bound by any theory, it is generally believed that there is a delayed correspondence between the subcutaneous glucose level and the blood glucose level. In general, it is believed that subcutaneous glucose level reflects blood glucose level of about 10 minutes ago.

One of the benefits of real-time monitoring of the glucose level is the ability of these devices to have an alarm system to alert the patient of a potentially dangerous situation, e.g., hypoglycemia. Such an alarm system can be programmed to provide a warning (i.e., alarm) signal to the patient when a potentially dangerous condition arises. The alarm signal can be of any of the known sensory eliciting alarm system such as tactile (e.g., touch), smell, visual, and/or audible. In some embodiments, the warning signal is audible, visible, tactile, or a combination thereof.

There are several factors that can be used to trigger the alarm (i.e., warning signal). In the case of a diabetic, the rate of glucose level change can be a cause for triggering the warning signal. Alternatively, the glucose level itself can trigger the warning signal regardless of the rate of glucose level change. For example, the receiver-controller device can be programmed to reduce or stop infusion of insulin when (a) the glucose level measured by the monitor is at about 130-150 mg/dl or lower and the rate of glucose level decrease as measured by the monitor is about 2 mg/dl-min or higher; (b) the glucose level measured by the monitor is from about 100 mg/dl to about 130 mg/dl and the rate of glucose level decrease as measured by the monitor is 1 mg/dl-min or higher; or (c) the glucose level measured by the monitor is about 70 mg/dl or less. It should be appreciated that the scope of the invention includes other glucose level and the rate of glucose level decrease and can change significantly depending on the response of each individual. Moreover, the glucose level and/or the rate of glucose decrease maybe modified as more data are collected and analyzed. Accordingly, in some embodiments the receiver-controller is programmable to allow modification of warning condition(s) that trigger either delivery of or stop delivery of the therapeutic substance.

In some instances the warning signal and the operation of the therapeutic substance delivery device can be operatively connected to stop or start the delivery of insulin. It should be appreciated, however, that the operation of the therapeutic substance delivery device need not be immediate when the warning signal is generated. In some instance, the operation of the therapeutic substance delivery device is delayed at least 10 min, 20 min, 30 min, or even an hour to provide an opportunity for the patient to take necessary action to manually abate the potentially dangerous situation, e.g., by manually testing the glucose level, by manually injecting insulin (for high glucose level), or by increasing the glucose level (for low glucose levels). In some embodiments, after the warning signal has been generated, unless the patient takes action within a prescribed time frame, e.g., 10, 20, 30, or 60 min (which in some cases can be revised or reprogrammed), the receiver-controller device operates the therapeutic substance delivery device automatically.

To prevent or reduce the risk of hypoglycemia, the receiver-controller device can be programmed to stop or reduce the operation of glucose infusion pump when (a) the glucose level measured by the monitor is at about 130-150 mg/dl or lower and the rate of glucose level decrease as measured by the monitor is about 2 mg/dl-min or higher; (b) the glucose level measured by the monitor is from about 100 mg/dl to about 130 mg/dl and the rate of glucose level decrease as measured by the monitor is 1 mg/dl-min or higher; or (c) the glucose level measured by the monitor is about 70 mg/dl or less. However, as mentioned above, these conditions can change depending on a particular individual. In some instances, the medical system can be programmed to be custom tailored to a particular individual. After reducing or stopping infusion of insulin, the receiver-controller device can be programmed to restart the full insulin infusion if no action is taken to reset the alarm within a prescribed time, e.g., about 2 hours or less, to prevent developing ketones or acidosis.

In some instances, if the glucose level increases at a relatively fast rate, e.g., ≥2 mg/dl, the receiver-controller can be programmed to administer an insulin bolus or at some other prescribed or programmable rate (e.g., increase in basal rate).

Communication (e.g., signals) to and from the monitoring device, the receiver-controller device, and the therapeutic substance delivery device can independently be through a wired connection or by a radio frequency (such as Bluetooth). In some embodiments, the signal to and from each component is by a radio frequency. In this manner, each component can be independently implemented without any changes to wiring to and from each device. Necessary wiring connections between devices and communication between devices using radio frequency are well known to one of ordinary skill in the electronics art. One of the advantages of using the Bluetooth technology is its relatively short range communication which significantly reduces interference with other nearby electronic devices. Furthermore, the Bluetooth technology allows communication between only selected devices, thereby reducing interference of medical system from other Bluetooth devices or other electronic devices.

The therapeutic substance delivery device comprises an electronic control circuitry that is configured to deliver a therapeutic substance to a patient at programmed or programmable rate. Insulin infusion pumps that can deliver various amount of insulin are well known in the art, for example, MMT2001 Implantable Pump System (by Minimed Inc., of Northridge, Calif.) as well as those described in U.S. Pat. No. 6,958,705, assigned to Metronic Minimed Inc.), as well as other commercially available insulin pumps.

The receiver-controller device receives the signal from the monitoring device and determines the need for administering the therapeutic substance. Alternatively, the receiver-controller device receives the signal from the monitoring device and determines the need to reduce (e.g., by 30%, 50% or 70%) or stop administering the therapeutic substance. That is, the receiver-controller can be programmed to start and/or stop administering the therapeutic substance. In many embodiments, the receiver-controller comprises a central processing unit (CPU) that is used to process the information (i.e., signal it receives from the monitoring device) and to control the operation of therapeutic substance delivery device. In some embodiments, the receiver-controller device is programmable. This allows one to revise or reconfigure warning condition(s), thereby allowing one to custom tailor the warning condition(s) to a particular subject. Ability to program warning condition(s) is helpful in cases where a set of condition(s) for warning condition(s) can change due to additional data gathering and/or due to change in the subject's physical conditions.

After receiving the signal (i.e., information) from the monitoring device, the receiver-controller device compares the information to a set of data (or parameters) and controls the therapeutic substance delivery device accordingly. As stated above, control of the therapeutic substance delivery device can be achieved by transmitting appropriate radio frequency (e.g., wireless unit) or electricity (e.g., wired unit) to cause the therapeutic substance delivery device to administer (i.e., deliver) or stop administering the therapeutic substance. The set of data (or parameters) can be programmed into the receiver-controller device or can be stored permanently in the receiver-controller device. Ability to program or reprogram the receiver-controller device allows the set of data (or parameters) to be updated as further data is gathered.

The receiver-controller can also include a storage device to store a set of data (or parameters). The storage device can be in the form of read-only memory (ROM), programmable read-only memory (PROM), electrically programmable read-only memory (EPROM), random access memory (RAM), hard disk, a removable storage device (e.g., CD, DVD, mini-CD, mini-DVD, flash memory), etc.

Additional objects, advantages, and novel features of this invention will become apparent to those skilled in the art upon examination of the following examples thereof, which are not intended to be limiting.

EXAMPLES

The Diabetes Control and Complications Trial (DCCT) showed that glucose control in the closer-to-normal range ("tight" glycemic control) reduced the likelihood of the eye, kidney, nerve and cardiovascular complications of diabetes. Increasing the frequency of glucose monitoring was an important aspect of attaining improved glucose control in the DCCT. The "tight" glycemic control group in the DCCT had a delay in the development of the eye, kidney, nerve and cardiovascular complications of diabetes by more than 50%. As a result, physicians have attempted to keep children and adults in very "tight" glucose control. Unfortunately, the DCCT study also showed that the incidence of severe hypoglycemia was three times higher in the intensively treated group compared with the standard treatment group. Intensively treated subjects averaged one severe hypoglycemic episode every 1.6 years (62 per 100 patient years). Further, in the adolescent portion of the DCCT, the risk for severe hypoglycemia was even greater with one episode every 1.17 years (85.7 per 100 patient years). In the DCCT, 55% of the severe lows occurred during the sleep hours. One report in children found 75% of severe lows to occur during the nighttime hours.

Use of the MiniMed Continuous Glucose Monitoring System™ (CGMS) has demonstrated a surprisingly frequent incidence of significant hypoglycemia occurring at night. Amin, et al. reported an average nightly duration of hypoglycemia (<60 mg/dl) of 3.3 hours, which occurred during 51% of monitored nights, and Ludvigsson, et al. also reported hypoglycemia (<55 mg/dl) occurring during 40% of nights with an average duration of 2.2 hours. Kaufman, et al. reported glucose values <50 mg/dl on 35% of nights for an average duration of 2.35 hours, and Boland, et al. reported glucose values <60 mg/dl on at least one night in three for an average duration of 1.45 hours. These observations were made with the original MiniMed sensor which had a tendency to read low during the night. This sensor problem was largely corrected with the introduction of the MiniMed "Gold" continuous monitoring system in 2002.

The MiniMed Gold system was used to study the incidence of nocturnal hypoglycemia in 19 toddlers who were studied for 334 nights when the sensor was providing optimal results. On 33% of the nights glucose values were <60 mg/dl with a mean duration of 72 minutes. The high frequency and duration of nocturnal hypoglycemia has been confirmed in Clinical Research Center (CRC) studies where frequent laboratory reference glucose values were obtained. For example, in a DirecNet study of exercise induced nocturnal hypoglycemia, children who did not exercise had a 28% incidence of nocturnal hypoglycemia (glucose less than 60 mg/dl) and those who exercised had a 48% incidence of nocturnal hypoglycemia. In a recent study of bedtime snacks and nocturnal hypoglycemia, on nights when adult subjects did not have a snack, 57% became hypoglycemic (<70 mg/dl) with an average duration of hypoglycemia of over 2.5 hours. In this study the duration of hypoglycemia was as long as 8.75 hours.

"Moderate hypoglycemia" is defined as "an event requiring the assistance of another person"; in those <6 years old, it is defined as "events with obvious neuroglycopenia manifesting as confusion or drowsiness that required immediate treatment but where the child could be treated with oral carbohydrate and did not need glucagon treatment."

"Severe hypoglycemia" is defined by a seizure, loss of consciousness, severe neurological impairment, or neurological impairment suggestive of hypoglycemia and requiring an emergency department visit or hospitalization.

One of the major risk factors for a severe hypoglycemic event is a previously experienced severe hypoglycemic event. For this reason the study includes youth who have had a severe hypoglycemic episode in the past 18 months, and who are therefore at increased risk for having another one. It has been found that once a family has been through a severe hypoglycemic event; it is often several years before they are again willing to aim for tight glycemic control. Thus initial HbA1c values for the patients in the study likely is above the target range. The fear of severe hypoglycemia remains one of the major impediments to attaining optimal glycemic control. It is believed that this experiment is the first concentrated effort to lower HbA1c values in this group.

Real-time continuous glucose monitoring is becoming available to the general public with the FDA approval of the MiniMed Guardian™ and the DexCOm™ STS™ for adults. One of the major benefits of real-time glucose monitoring is the ability of these devices to have alarms for hypoglycemia. For a real-time alarm to be effective, it must awaken a sleeping subject. The first FDA-approved real-time glucose monitor was the GlucoWatch™. To determine if the alarm function on the GlucoWatch was effective in awakening children while they were sleeping, an infrared camera was used to videotape them throughout the night in CRCs. During this admission, reference glucose values were obtained every ½ hour to document hypoglycemia. In this study using the GlucoWatch, 71% of youths wearing the watch did not respond to nighttime alarms, placing these patients at a risk for nocturnal hypoglycemia despite wearing a real-time continuous glucose sensor. It was also observed that children wearing the Navigator fail to respond to alarms at night. One possible correction of this problem is to remove the patient from the loop (so they do not have to awaken) and have the sensor send a signal to the pump so that it will stop infusing insulin when pending or real hypoglycemia has been reached and the patient has not responded to alarms.

When insulin infusion is stopped for two hours, there is minimal risk of the patient developing ketones or acidosis. It has been demonstrated that turning off an insulin pump for two hours does not result in diabetic ketoacidosis (DKA). In some studies, the CSII pumps were purposely turned off for periods of 4 and 5 hours, with a gradual increase in ketone levels after 2 hours to the upper normal range. No cases of DKA occurred in these studies. In another study, the CSII was discontinued during 2 hours of exercise (a stimulus to increase production of counter regulatory hormones and possibly of blood ketones). In all three studies there was a gradual increase in blood glucose (BG) levels when the CSII was discontinued.

The Navigator continuous glucose monitor is available from Abbott. This sensor uses a wired enzyme technology, and is designed to measure BG levels in a range of 20-500 mg/dl. The sensor is inserted subcutaneously and measures interstitial glucose levels. In human studies, the interstitial glucose levels generally lag behind the BG levels by 3 to 13 minutes. The Navigator provides a glucose reading every 60 seconds (or 1440 readings a day). Each sensor is designed to provide readings for up to 120 hours. It has alarms for hypoglycemia and hyperglycemia as well as for projected high and low glucose values, which can be adjusted by the user. The Navigator also has a trend arrow indicating the glucose rate of change (>−2 mg/dl/min, −2 to −1 mg/dl/min, no change, +1 to 2 mg/dl/min, and >+2 mg/dl/min). The sensor requires calibration values to be entered 4 times during the 5 day sensor wear at approximately 10, 13, 29 and 81 hours. The values are entered directly into the Navigator which has a FreeStyle BG meter built into the unit.

One of the steps in being able to reduce or discontinue CSII is to develop algorithms (or parameters) to safely reduce or discontinue insulin therapy for pending hypoglycemia. For example, if glucose levels are falling rapidly (i.e. >−2 mg/dl/min), a safe level to discontinue CSII might be somewhere between 100 and 130 mg/dl. In contrast, if glucose levels are not changing, it might only be necessary to discontinue CSII if the glucose levels fall below 70 mg/dl. An additional factor that the algorithms (or parameters) may consider is the remaining "insulin on board." It may be necessary to decrease or turn the pump off at a higher glucose level if more insulin is still present.

Once the algorithms (or parameters) for reducing or discontinuing CSII (determining the appropriate time, based on rate of glucose decrease, for the CGM to alarm) are developed, the CGM can be used to decrease or turn off the CSII (e.g., for up to 2 hours) anytime the CGM alarms for a period of 10 minutes without a response from the wearer. If the person initially hears and responds to the alarm by doing a BG measurement, then the CSII may continue uninterrupted. If after 10 minutes there is no response to the alarm, the CSII may suspend basal insulin for up to two hours. If the subject does respond to the alarm at any point after the insulin suspension and enters a BG value into the monitor that is above 70 mg/dl, the subject may then be able to restart the CSII. After two hours, the CSII may again resume the usual basal insulin infusion whether the wearer has responded to the alarm or not. This type of system may be especially valuable in the nighttime hours given the low response rate of children to alarms.

This example incorporates elements of in-patient and out-patient studies of the CGM (e.g., Abbott Diabetes Free-Style Navigator) in youth with diabetes using CSII. Direc-Net investigators have developed an algorithm for real-time and retrospective use of CGM data by clinicians and patients for optimizing glycemic control. Further studies can be conducted to test and refine the algorithm that can then be utilized.

To obtain a baseline assessment of glycemic variability, the Navigator used during the first week was blinded so subjects could not view the data from the sensor. Subjects returned for a 24-hour CRC admission approximately one week (7-12 days) after the enrollment visit and at that time underwent an exercise session as previously described. Outpatient follow-up visits were performed at 1, 3, 7, and 13 weeks after the CRC admission, and then every 3 months. A very similar protocol is used for the subjects in the final stage of the proposed study.

The present inventors have found that there was considerable variation in insulin sensitivity between subjects. Accordingly, it was found that the glucose level and the time the insulin is reduced or turned off should be individualized (e.g., varied from person to person). Alternatively, a set of ranges for insulin sensitivity can be set on the system (e.g., in the continuous glucose monitor (CGM) or in the insulin pump). This can be used to set individual's sensitivity based on an "Increased-Basal" test that they do in their home or elsewhere. For example, if a person gave 125% of the usual basal insulin in the fasting state and fell rapidly (1-3 hrs) to a low glucose level, they would be "very insulin sensitive" (e.g. a "1" setting). If they did not decrease their glucose levels significantly with 90-120 minutes of 125 or 150% of basal insulin levels, they might be classified as "insulin-resistant" (perhaps a "5" setting). The algorithm for an "insulin sensitive" person would decrease/stop insulin delivery at a higher glucose level (e.g. 100 mg/dl) than for an "insulin resistant" person (e.g. 80 mg/dl). The "insulin sensitive" person might also have need for a greater reduction (e.g. 100%) of insulin and for a longer time (e.g. 90 minutes). In contrast, an "insulin resistant" person might only need a 50% reduction in insulin for 60 minutes. It is likely that the state of insulin sensitivity could also vary within the same person. A person who is normally "insulin sensitive" may have a cold or other infection, or their monthly menses, and become more insulin resistant. Therefore, it is desirable to have the ability to change the level of insulin sensitivity as a feature of the CGM/pump system.

Results

The accuracy of the Navigator was similar during outpatient and inpatient assessments (median relative absolute difference 14% and 12%, respectively) and sensors performed well up to 5 days. Subjects averaged 128 hrs/wk of Navigator use during weeks 1-2 and 91 hrs/wk during weeks 6-7 (p<0.001). Two subjects withdrew and 2 subjects had a severe skin reaction. For the 28 subjects completing the 13-week visit, HbA1c values dropped from 7.1±0.6% at baseline to 6.9±0.7% at 7 weeks to 6.8±0.7 at 13 weeks (p=0.02). The mean drop in HbA1c was 0.0±0.5% for the 12 subjects whose baseline HbA1c was <7.0% and 0.5±0.6% for the 16 subjects whose baseline HbA1c was ≥7.0%. The mean glucose concentration was 176±25 mg/dl at baseline, dropped to 160±21 mg/dl during weeks 7-8 and remained steady through week 13 (p=0.02). As shown in Table 1, the percentage of Navigator values in the target range (70-180 mg/dl) rose from 52% at baseline to 60% during weeks 7-8 and remained at that level throughout the rest of the study (p=0.01). Hyperglycemic levels also decreased during the 13-week period (Table 1). Glycemic variation as measured by the SD and MAGE also decreased during the study period. Hypoglycemic values did not change dramatically, possibly because of more frequent alerts.

TABLE 1

|  | Blinded N = 29 | Weeks 7-8 N = 26 | Weeks 11-13 N = 25 |
|---|---|---|---|
| % Values 71-180 mg/dl | 52% | 60% | 61% |
| Hypoglycemia | | | |
| % values ≤70 mg/dl | 4.6% | 5.1% | 4.8% |
| % values ≤60 mg/dl | 2.1% | 2.4% | 2.0% |
| % values ≤50 mg/dl | 1.05% | 1.05% | 0.65% |
| Area over the Curve | 0.52 | 0.56 | 0.45 |
| Hyperglycemia | | | |
| % values >180 mg/dl | 43% | 36% | 35% |
| % values >200 mg/dl | 34% | 27% | 26% |
| % values >250 mg/dl | 17% | 11% | 11% |
| % values >300 mg/dl | 6.7% | 3.3% | 2.9% |
| Area under the Curve | 29 | 20 | 19 |
| Glucose Lability | | | |
| SD (mg/dl) | 58 | 52 | 52 |
| MAGE (mg/dl) | 129 | 113 | 117 |
| Mean absolute rate of change | 0.83 | 0.83 | 0.78 |

Both patients (≥7 years old) and their parents reported high overall satisfaction with the Navigator on the CGM Satisfaction Scale at 13 weeks with average item scores of 3.8 and 3.8, respectively, on a 5-point Likert scale. 82% of patients and 90% of parents agreed or strongly agreed that the Navigator made adjusting insulin easier and 72% and 87% of patients and parents agreed or strongly agreed that the Navigator helped prevent problems rather than fixing them after they have happened. At 13 weeks, all of the patients and all but 1 of the parents agreed that the DirecNet Applied Treatment Algorithm (DATA) gave good clear directions for how much insulin to give.

Determining Various Parameters

This study is subdivided into the following Stages (1, 2A, 2B, and 3):

| Study Stage | Duration | Purpose |
|---|---|---|
| Stage 1 | 1 Year | Inpatient study for the purpose of algorithm development* |
| Stages 2A and 2B | 1 Year | Efficacy and safety evaluation of Stage 1 algorithm in CRC and home-setting* |
| Stage 3 | 2 Years | Randomized Clinical Trial in the home setting+ |

*Low-risk population (no previous severe hypoglycemic event in past 18 months)
+High-risk population (having a severe hypoglycemic event in past 18 months)

Enrollment includes 20 subjects in Stages 1 and 2, and 30 subjects in Stage 3 in each of the age groups of 3.0 to <13.0 years old, and 13.0 to <31.0 years old for a total of 40 subjects in Stages 1 and 2 and 60 subjects in Stage 3. Subjects include both males and females to achieve an approximately equal sex distribution in each age group.

Subjects for all three stages are recruited from the database queries done at each participating center that identify eligible patients. After identification of potential subjects, the patients are contacted by phone to invite each to a study-specific clinic visit. The study is outlined and, if the subject and parent/guardian express interest, is presented in detail.

Inclusion/Exclusion Criteria

The following Inclusion and Exclusion Criteria were used in all three stages. Inclusion parameters are: 1) Clinical diagnosis of type 1 diabetes and using daily insulin therapy for at least one year. The diagnosis of type 1 diabetes can be based on the investigator's judgment; C peptide level and antibody determinations are not necessary; 2) Age 3.0 years to less than 31.0 years old; 3) Subject has used a downloadable insulin pump for at least 6 months; 4) Parent/guardian and subject understand the study protocol and agree to comply with it; 5) Subjects >7.0 years old and primary care giver (i.e., parent or guardian) comprehend written English; 6) Subject has a home computer with email access; 7) For females, subject not intending to become pregnant during the study; 8) No expectation that subject is moving out of the area of the clinical center during the study; 9) Informed Consent Form signed by the parent/guardian and Child Assent Form signed by subjects ages 7 to 17 years; and 10) For Stages 1 and 2, subjects should have had a severe hypoglycemic event, as described in Background, within 18 months of enrollment. For Stage 3, it is desirable that the subjects have had a severe hypoglycemic event within 18 months of enrollment. Exclusion parameters are: 1) The presence of a significant medical disorder that in the judgment of the investigator affects the wearing of the sensors or the completion of any aspect of the protocol; 2) The presence of any of the following diseases: • Asthma if treated with systemic or inhaled corticosteroids in the last 6 months; • Cystic fibrosis; • Other major illness that in the judgment of the investigator might interfere with the completion of the protocol Adequately treated thyroid disease and celiac disease do not exclude subjects from enrollment; 3) Inpatient psychiatric treatment in the past 6 months for either the subject or the subject's primary care giver (i.e., parent or guardian); and 4) Current use of oral/inhaled glucocorticoids or other medications, which in the judgment of the investigator may be a contraindication to participation in the study.

Stage 1 of this example focuses on algorithm development and consists of a series of 24-hour, openly-randomized, CRC-based, inpatient studies with a total of 40 subjects.

Prior to enrollment in Stage 1, all parents and subjects need to sign an Informed Consent Form, an Assent Form (ages 7-17) and an authorization form for release of personal information. On the day of enrollment, all subjects have an HbA1c and a physical. In the clinic, study personnel inserts a Navigator CGM sensor and instructs the subject to wear it for 1-3 days until the admission at the CRC. They are also given instructions for calibrating and using the Navigator. Subjects are able to view continuous glucose data from the sensor, and alarms for hypoglycemia (<70 mg/dl) are activated. The subjects are instructed to complete at least four BG measurements a day (which are displayed on the screen) using the FreeStyle® meter built into the Navigator. Subjects in Stage 1 participates in insulin suspension algorithm development under two testing conditions: 1) a rapid decline in glucose levels and 2) a slow decline in glucose levels (see Table 2 below for one example).

TABLE 2

| Group | Sub-group | Glucose rate of change | Pump suspension target |
|---|---|---|---|
| Slow Glucose Decline | A | 0 to −1 mg/dl/min | 70 mg/dl |
| | B | −1 to −2 mg/dl/min | 90 mg/dl |
| Rapid Glucose Decline | C | −2 to −3 mg/dl/min | 110 mg/dl |
| | D | >−3 mg/dl/min | 130 mg/dl |

In Stages 1 and 2A, all subjects will enter the CRC in the morning of Day 1 and will be randomized to either a slow (subgroups A or B) or rapid (Subgroups B or C) one to occur on the afternoon of Day 1 and the second to occur, under fasting conditions, on the morning of Day 2.

Each of the four "glucose-rate-of-change" conditions is tested in 20 total subjects (10 at each center). The afternoon of CRC day 1 and the morning of CRC day 2 are used to assess insulin suspension algorithms under these test conditions. A randomization for each subject is performed to determine when during the CRC admission each test condition are evaluated and which specific "glucose-rate-of-change" test conditions are to be used. One test is three hours post-prandial and one is in the fasting state.

Stage 1 involves a 24-hour admission to the CRC. All subjects wear an insulin pump and the Navigator (sensor inserted 1-3 days previously in the clinic). Subjects are admitted to the CRC at 10:00 AM. All subjects have an intravenous (IV) catheter inserted to allow for venous BG measurements and to provide access for IV dextrose, should it be needed. The first period of randomized testing begins three hours after the noon meal. After the first period of testing, subjects consume a standardized evening meal±a bedtime snack and are allowed to dose their insulin as they would in a home setting. After 10:00 PM, subjects are not allowed to consume any meals or snacks unless they experience hypoglycemia, defined as hypoglycemia symptoms accompanied by a BG<70 mg/dl.

From 12:00 MN to 8:00 AM, subjects have their venous BG measured hourly using the FreeStyle meter built into the Navigator. In the event a subject's BG falls below 70 mg/dl, venous BG measurements are conducted every 10 minutes until the subject's BG rises above 70 mg/dl. Based on the Navigator and venous FreeStyle glucose readings, subjects' basal rates is adjusted from 4:00 AM to 8:00 AM to aim for 8:00 AM glucose target values between 150 and 200 mg/dl, which is verified by a fingerstick BG on the Navigator's FreeStyle meter. At 8:00 AM, or when the subject is within the glucose target range while still fasting, the second "glucose-rate-of-change" is induced using additional basal CSII (see Table 2 above). The rate of change is followed by the minute-to-minute glucose values displayed on the Navigator and by venous blood (via IV) Freestyle glucose values every 30 minutes.

When the subject has met the pump suspension target glucose (Table 2—above), which is verified by a FreeStyle BG measurement, the study nurse or physician manually suspends the CSII basal insulin for a period of up to 2 hours. During this "2-hour post-insulin suspension" observation period, study staff continuously monitors Navigator glucose values. Venous FreeStyle BG values are measured every 10 minutes and venous blood ketones are measured every 30 minutes (both via IV) to determine if any further reduction in glucose levels occurs and if the subjects can safely go two hours with CSII discontinued. If the Navigator glucose level falls below 60 mg/dl and is verified with a fingerstick BG measurement, the subject is treated with oral or IV glucose. If the Navigator glucose level exceeds 300 mg/dl and is verified by a fingerstick BG measurement, study staff restarts CSII and a standard correction dose is administered.

If the subject meets either of these conditions (<60 or >300 mg/dl), then the "2-hour post-suspension" observation period is terminated early.

Upon completion, or early termination, of the "2-hour post-suspension" observation period, CSII is reinstituted manually. The subject is then allowed to eat a meal. The subject remains at the CRC for a 2-hour observation. During this 2-hour follow-up, study staff monitors Navigator glucose values continuously, and venous BG and blood ketone levels are measured every 30 minutes. Subjects are discharged after completion of this final observation period. The final development of the optimal algorithms for use in Stage 2 is developed using the data from Stage 1.

Stage 2: Testing of the Closed Loop System with Preprogrammed Algorithms

Stage 2A is a series of 24-hour, openly randomized, CRC-based, inpatient studies with a total of 40 subjects per study. This trial evaluates the safety and efficacy of the prototype closed loop system algorithms developed in Stage 1.

Stage 2B is an optional 3 to 9 month, nonrandomized, outpatient feasibility study available to all 40 subjects who participated in the Stage 2A study in which they use the prototype closed loop system in the home setting.

All subjects who participated in Stage 1 are offered the opportunity to participate in both Stages 2A and 2B. Prior to enrollment in these stages, all parents and subjects sign an Informed Consent Form, an Assent Form (ages 7-17) and an authorization form for release of personal information. On the day of enrollment, all subjects have an HbA1c, a physical and are randomized to a Test group or a Control group. In the clinic (1-3 days prior to CRC admission), each Test group subject's personal insulin pump and infusion set are removed and replaced with those of the closed loop system (Deltec Cozmo insulin pump). Both groups (Test and Control) insert two Navigator CGM sensors in the clinic and are instructed to wear them for 1-3 days until the admission at the CRC. They are also given instructions for calibrating and using the Navigator. Subjects are not able to view continuous glucose data from the Navigator (blinded) until admission to the CRC. The subjects are instructed to complete at least four BG measurements a day (which is displayed on the screen) using the FreeStyle® meters built into the Navigators. Study personnel provides education on use of the Deltec Cozmo pump for the Test group. Subjects in Stage 2A evaluates the safety and efficacy of the preprogrammed algorithms, derived from the Stage 1 trial, under two test conditions: 1) a rapid decline in glucose and 2) a slow decline in glucose (Table 2—above). The afternoon of CRC day 1 and the morning of CRC day 2 are again used to evaluate the algorithms under these test conditions. As in Stage 1, a randomization for each subject is performed to determine when during the CRC admission each test condition is evaluated. For Stage 2B, those participants who are interested are allowed to continue the use of the prototype closed loop system (Test group) or their own pump and a Navigator (Control group) in a 3 to 9 month home setting (after completing the Stage 2A CRC admission).

The CRC admission in Stage 2A follows the similar protocol as outlined above for Stage 1 with the following exceptions: (1) at approximately 3:00 PM on day 1 and 8:00 AM on day 2, or when the subject is within the glucose target range at each test period, communication between the Navigator and insulin pump in the Test group is enabled prior to inducing the glucose rates of change; (2) the closed loop system, in response to the preprogrammed algorithms developed in Stage 1, is responsible for suspending delivery of basal insulin (rather than manually by the study staff) for up to 2 hours in the Test group; (3) the Control group do not have their basal insulin discontinued after the Navigator alarms for pending or real hypoglycemia. Once the subject has met the "glucose-rate-of-change" they were assigned to, the study staff monitors venous BG levels every 30 minutes for the next 2 hours. As with all subjects, the Control group is treated with oral glucose if glucose levels drop below 60 mg/dl (verified by a fingerstick blood glucose test done on the FreeStyle meter) and receives a standard correction dose if glucose levels rise above 300 mg/dl. Upon completion of the 2-hour observation period, the subject's basal rate is returned to normal. Study staff ensures that the subject's glucose levels do not continue to drop; (4) for the Test group, in the event of an early termination (due to glucose levels less than 60 or greater than 300 mg/dl) of the "2-hour post-suspension" observation period, CSII is reinstituted manually as indicated by the study staff. If subjects complete the full "2-hour post-suspension" observation period, CSII is reinstituted automatically by the prototype closed loop system; (5) the availability of two functioning Navigators allows evaluation of differences in algorithm decision making resulting from variations between CGMs.

Stage 2B is an optional 3 to 9 month, outpatient, feasibility study, available to all 40 low-risk subjects who participated in Stage 2A. For this stage of the study, the subjects continue using (in the home setting) the devices they were randomized to in Stage 2A. There is no CRC admission for this portion of the study. Any subject who participated in Stage 2A, and is interested in participating in this optional Stage 2B study, undergoes an additional educational visit. During this visit, subjects receive additional training and guidance on how to use the Navigator, and for the Test group, prototype closed loop system in the home setting. All subjects receive instructions for downloading and emailing both Navigator and pump data to the study staff. Subjects return to the clinic for monthly follow-up visits to allow for assessment of the skin at the Navigator sensor sites, an assessment of the subjects understanding and use of the algorithms designed for treatment based on Navigator readings and trends, as well as treatment recommendations based on the downloaded data. Any events that resulted in the discontinuation of the insulin pump due to pending hypoglycemia (Test group) is also recorded.

Inclusion and Exclusion criteria for stage 3 remains similar to Stages 1 and 2 with one exception being (Inclusion #10) that eligible subjects must have had a severe hypoglycemic event, as defined above, in the past 18 months. In addition, subjects >18 years of age often have an inability to recognize the signs and symptoms of hypoglycemia (hypoglycemic unawareness). These subjects are all at a higher risk for future severe hypoglycemic events.

A nine-month, randomized, parallel group study of 60 subjects, in which a Test group of 30 subjects wear a closed loop system for 9 months and a Control group of 30 subjects wear the Navigator and CSII without communication between the two devices. After 1 year (~3 months for entry), the Control group is also provided with the opportunity to use the prototype closed loop system for a period of 9 months. This study takes place at two centers. Each center enrolls 15 test subjects and 15 control subjects for a total of 60 subjects. The potential subjects are identified by the clinic physicians and nursing staff. Eligibility is assessed by the Inclusion and Exclusion Criteria listed above with the exception as noted.

Prior to enrollment, all parents and subjects sign an Informed Consent Form, an Assent Form (ages 7-17) and an authorization form for release of personal information. On the day of enrollment, all subjects have an HbA1c and a physical. The PedsQL Questionnaire and the Fear of Hypoglycemia Questionnaire are completed by the parent/guardian and the subject (if ≥9 years old). The study personnel supervises the subject or parent inserting the Navigator sensor in the clinic and instructs the subject or parent to insert a second sensor at home in 5 days. The subjects are instructed to complete at least four BG measurements a day using the FreeStyle meter built into the Navigator. They are also given instructions for calibrating the Navigator. To obtain a baseline assessment of glycemic variability, the Navigator used during the first week are blinded so subjects are not be able to view the data from the sensor, and alarms are not activated. Subjects are then randomized to either the Test group or the Control group.

All subjects return for an overnight admission at the CRC one week (7-12 days) after the enrollment visit. At this visit, Navigator sites are evaluated, the pump and the Navigator are downloaded and treatment recommendations are made. The subject's Navigator is then un-blinded so that real-time glucose values can be seen. The hypoglycemia alarm is set to go off according to the algorithm developed in the initial stages of this study. The hyperglycemia alarm is set to go off when the glucose level goes above 300 mg/dl. All fingerstick and venous BG measurements are done using the FreeStyle meter built into the Navigator. The subjects and parents receive extensive education on use of protocol-developed algorithms for changes to diabetes management based on the downloaded Navigator data as well as projected glucose levels as indicated on the Navigator. The study nurse also instructs the subject and parent on the use of the Navigator. In addition, they are given software and instructions for downloading the Navigator and their insulin pump. All subjects have an intravenous catheter inserted to allow for venous BG measurements and to provide access for IV dextrose, should it be needed.

Those in the Test group receive the Navigator/Cozmo closed loop system and receive training on its use. The system is programmed to alarm and then suspend insulin delivery for up to 2 hours if projected hypoglycemia levels, as determined by the algorithms developed in the initial stage, are detected for a period of 10 minutes or more. When the Navigator alarms for predicted hypoglycemia, venous BG measurements are done every 10 minutes using the Navigator's FreeStyle meter until a low glucose level is no longer predicted. The hypoglycemia alarm continues during this two-hour period if the risk for hypoglycemia continues. The same procedure is followed if the algorithm again predicts impending hypoglycemia. If the BG level goes below 60 mg/dl at anytime on the FreeStyle meter, the subject is treated with 15-30 grams of oral glucose. Additional oral glucose is given in 15-gram increments every 15 minutes until the BG level is above 70 mg/dl. If the subject is unable to take oral glucose, 25% IV Dextrose is available at the bedside and is given (1-2 cc/Kg body weight) at the discretion of the physician or study nurse.

Those in the Control group use the Navigator CGM and remain on their own insulin pump. If the subject's Navigator hypoglycemia alarm goes off, BG measurements are done using the same procedure as for the Test group. Guidelines for treatment with oral glucose or IV dextrose are the same as for the Test group (above).

During the admission, if the hyperglycemia alarm goes off, a fingerstick BG measurement is done and when the BG is above 300 mg/dl, a correction bolus according to each subject's standard correction factor is given, CSII is manually restarted if this occurs during the 2 hour suspension period and the BG is checked again in two hours.

During the CRC admission, subjects in both groups follow an afternoon exercise session as previously described by the DirecNet group. This more closely replicates the home situation. It has been shown that during the sleeping hours after an exercise session, children with type I diabetes (TID) spend more time in the hypoglycemic range (<70 mg/dl) when compared to a sedentary afternoon. This admission allows for a controlled environment for direct observation of the function of the augmented pump with the Navigator. Starting at 9 pm, venous BG (from the IV) is measured with the FreeStyle meter in the Navigator every hour until 7 am.

The subjects eat breakfast at the CRC and the study nurse then reviews instructions for each subject according to the guidelines set for their group assignment (Control or Test) before discharge. They are instructed to download the Navigator and their insulin pump on a weekly basis and email the files to the study nurse each Sunday. In addition to the hypoglycemia and hyperglycemia alarms, the alarms for impending hypoglycemia and hyperglycemia are also set. The subject and/or parent/guardian must show proficiency on the use of the Navigator, and for the Test group, the prototype Navigator/Cozmo pump system. They are also quizzed on goals for glucose levels, which varies by age. Necessary supplies (Navigator sensors and batteries, and FreeStyle test strips) are given to each subject. Appointments are made for the initial follow-up phone contact and the 7-week follow-up visit to the clinic.

Diabetes Management Follow-Up Visits for Both Groups

Phone contacts are made with all subjects at 2, 4, 8, 10, 16, 22, 28, and 34 weeks (±3 days) following the enrollment visit (Table 3—below). The primary purpose of the phone calls are to review the subject's diabetes management and make alterations as needed. The downloaded Navigator data have been emailed to the clinic before the call for review by the investigator and/or study nurse. Subjects provide diet data as well as information regarding any illnesses or stressful events. The subjects also have their understanding and use of the algorithms assessed.

Follow-up clinic visits are completed at 7, 13, 19, 26, and 39 weeks after the enrollment visit (Table 3—below). The visit windows are ±3 days at week 7 and ±1 week for weeks 13, 19, 26, and 39. At each visit, the Navigator and the insulin pump are downloaded and diabetes management are reviewed. An assessment of the duration of time spent within the hypoglycemic range (<70 mg/dl) are determined from the downloaded data and reviewed with the Control and Test subjects. Treatment recommendations are made based on the downloaded data. Areas where the Navigator was worn are assessed, as well as the subject's understanding and use of the algorithms. HbA1c values are measured using the DCA 2000 at all follow-up visits. For the Test group, the pump printout indicates any events in which the pump automatically shut off due to continuously low or rapidly decreasing glucose levels. This information is documented and is one of the major outcome of this study. At the 13, 26, and 39-week visits, a standard three-month physical is also performed. At the final, 39-week visit, the two psychosocial questionnaires are also administered.

TABLE 3

The following table outlines the Stage 3 visit schedule: (Both groups will follow the same schedule)

| Visit | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Week | 0 | 1 | 2 | 4 | 7 | 8 | 10 | 13 | 16 | 19 | 22 | 26 | 28 | 34 | 39 |
| Type (O = Office, P = Phone, H = Hospital) | O | H | P | P | O | P | P | O | P | O | P | O | P | P | O |
| Time required (in hours) | 2.5 | 24 | 15 min | 15 min | 1 | 15 min | 15 min | 1 | 15 min | 1 | 15 min | 1 | 15 min | 15 min | 2.5 |
| Informed Consent | X | | | | | | | | | | | | | | |
| General Physical Exam | X | X | | | | | X | | | | X | | | | X |
| HbA1c (fingerstick) | X | | | | X | | | X | | X | | X | | | X |
| Review Navigator Data | | X | X | X | X | X | X | X | X | X | X | X | X | X | X |
| Review Pump Data | X | X | X | X | X | X | X | X | X | X | X | X | X | X | X |
| Adjust Insulin/Dosing Guidelines | X | X | X | X | X | X | X | X | X | X | X | X | X | X | X |
| IV Insertion | | X | | | | | | | | | | | | | |
| Hourly/10 min Venous Blood Glucose Measurements | | X | | | | | | | | | | | | | |
| Exercise Session | | X | | | | | | | | | | | | | |
| Complete Two Questionnaires | X | | | | | | | | | | | | | | X |
| Study Supplies Distributed | X | X | | | X | | | X | | X | | X | | | X |
| Collect Study Sensors/Study Devices | | X | | | X | | | X | | X | | X | | | X |

Outcome Measures, Sample Size and Statistical Considerations

The study enrolls 40 total subjects (20 subjects from each of the two centers) for Stages 1 and 2 and 60 total subjects (30 from each center) for Stage 3. This total number of subjects allows for a 15% dropout rate. In both Stages 1 and 2, the 40 subjects are randomized equally (1:1:1:1) into the four "Glucose-Rate-of-Change Groups," with each subject evaluating two of the four conditions. In Stage 3, the 60 test subjects are randomized in a 1:1 fashion to test and control groups, with 30 subjects per group (15 at each center). During the first 9 months of study, the 30 test subjects wear the closed loop system and the control subjects do not. During the second 9 months of study, test subjects have the option of continuing to use the device, and control subjects who are interested are also allowed to wear the device.

Stages 1 and 2:

The primary outcome measure of the first stage is the development of an algorithm to determine at what glucose level insulin delivery from a CSII pump is turned off according to the rate of decrease of glucose as indicated by the Navigator CGM as well as the amount of insulin "on-board" as determine by the pump. Primary outcome measure of the second stage is to determine the safety and efficacy of the functioning closed loop system with the incorporation of the algorithms developed in stage one in both the CRC and the home setting. In the initial DirecNet Navigator study, 27 of 30 (90%) subjects elected to continue to use the Navigator (10% dropout). This population is at a low-risk for severe hypoglycemia, therefore, it is too infrequent to analyze statistically (outcome 3 in Stage 3 below). However, the percent of values "in-range" and the percent of hypoglycemic values are analyzed as in the primary outcome for Stage 3 below. This shows if it is likely to be effective in the population at high risk for severe hypoglycemia (Stage 3) in improving these parameters.

Stage 3:

One of the outcome is to measure percent of Navigator-measured glucose values in the hypoglycemic ($\leq 70$ mg/dl) and euglycemic ranges (71-180 mg/dl). Preliminary data showed that $52\pm 10\%$ of glucose values were initially in the euglycemic range (71-180 mg/dl). After 13 weeks of Navigator use, $61\pm 10\%$ of glucose values were in the euglycemic range, demonstrating an increase of approximately 10% of glucose values in range. With 30 patients in each group and a 15% dropout rate, there is about 94% power to detect a 10% difference in values within range between the two groups with a 2-sided $\alpha=0.05$. Corresponding to this increase in percent of values in range, it is estimated that there is a decrease in the percent of hypoglycemic values ($\leq 70$ mg/dl). Preliminary data suggest approximately 5% of Navigator measured glucose values initially fall in this hypoglycemic range ($\leq 70$ mg/dl). 30 subjects per group, and a 15% dropout rate, allows 80% power to detect a difference between 5% of glucose values $\leq 70$ mg/dl in the control group and 1% of glucose values $\leq 70$ mg/dl in the test group with a standard deviation of 5%. The percent of time spent <50 mg/dl is also evaluated. It should be noted that the subjects in the initial Navigator pilot trial had not had a severe hypoglycemic episode in the 6 months prior to study participation.

Another outcome is HbA1c values in the test and control groups. The mean HbA1c value in this controlled study population is expected to be approximately 8.6%. With 30 subjects in each group, and a 15% dropout rate, there is about 94% power to detect a 1.0% difference in HbA1c when the pooled standard deviation is equal to 1.0%.

As an additional outcome, the number of moderate and severe hypoglycemic episodes are recorded.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A medical system comprising:
a monitoring device comprising an electronic control circuitry that is configured to monitor a rate of change in a selected state of a subject, wherein said monitoring device further comprises a telemetry system;
a therapeutic substance delivery device comprising an electronic control circuitry that is configured to deliver insulin to the subject; and
a receiver-controller device comprising an electronic circuitry that is configured to receive a signal generated by said monitoring device and is further configured to control the operation of said therapeutic substance delivery device based on the rate of change in the selected state of the subject as monitored by said monitoring device wherein said receiver-controller is configured to reduce or stop administering insulin then the glucose level decreases and to automatically resume delivery of insulin about 1 hour to about 2 hours after insulin delivery is reduced or stopped.

2. The medical system of claim 1, wherein said monitoring device monitors the rate of glucose level change in the subject.

3. The medical system of claim 2, wherein said therapeutic substance delivery device is configured to administer insulin to the subject based on the rate of glucose level change.

4. The medical system of claim 3, wherein said receiver-controller is configured to reduce or stop administering insulin when the glucose level decreases at a rate of 2 mg/dl-min or higher.

5. The medical system of claim 1, wherein said monitoring device measures the rate of subcutaneous glucose level change.

6. The medical system according to claim 1 further comprising an alarm system for providing a signal to the patient, wherein said receiver-controller is configured to reduce or stop administering insulin after a subject has been signaled by said alarm system and the subject has failed to take action responsive to said alarm.

7. The medical system according to claim 6 wherein said receiver-controller is configured to reduce or stop administering insulin after a subject has been signaled by said alarm system and the subject has failed to take action responsive to said alarm, wherein the delay to allow subject action following the signal is selected from the group consisting of about 10 minutes, about 20 minutes, about 30 minutes and about 1 hour.

8. The medical system of claim 1 wherein said receiver-controller is configured to automatically resume delivery of insulin according to the insulin sensitivity of the subject.

9. The medical system of claim 1 wherein said receiver-controller is configured to reduce or stop administering insulin to the subject when the glucose level is about 150 mg/dl or lower and the glucose level decreases at a rate of about 2 mg/dl-min or higher, the glucose level is from about 100 mg/dl to about 130 mg/dl and the glucose level decreases at a rate of from about 1 to about 2 mg/dl-min or higher, or the glucose level is about 70 mg/dl or lower.

10. The medical system of claim 1, wherein said receiver-controller is configured to reduce or stop administering insulin when the glucose level is about 70 mg/dl or lower.

11. A medical system comprising:
a monitoring device comprising an electronic control circuitry that is configured to monitor a rate of change in a selected state of a subject, wherein said monitoring device further comprises a telemetry system;
a therapeutic substance delivery device comprising an electronic control circuitry that is configured to deliver insulin to the subject;
a receiver-controller device comprising an electronic circuitry that is configured to receive a signal generated by said monitoring device and is further configured to control the operation of said therapeutic substance delivery device based on the rate of change in the selected state of the subject as monitored by said monitoring device; and
an alarm system in communication with the receiver-controller for providing a signal to the patient, wherein said receiver-controller is configured to reduce or stop administering insulin to the subject when the glucose level decreases and after the subject has been signaled by said alarm system and the subject has failed to take action within at least about 10 minutes responsive to said alarm signal.

12. The medical system of claim 11 wherein the period of time that the subject has failed to take action is selected from the group consisting of about 10 minutes, about 20 minutes, about 30 minutes, and about 1 hour.

13. The medical system of claim 11, wherein said monitoring device monitors the rate of glucose level change in the subject.

14. The medical system of claim 11, wherein said monitoring device monitors the rate of subcutaneous glucose level change.

15. The medical system of claim 11 wherein said receiver-controller is configured to automatically resume delivery of insulin according to the insulin sensitivity of the subject.

16. The medical system of claim 11, wherein said receiver-controller is configured to reduce or stop administering insulin when the subject has failed to take action within at least about 10 minutes responsive to said alarm signal and the glucose level is about 150 mg/dl or lower and the glucose level decreases at a rate of about 2 mg/dl-min or higher, the glucose level is about 130 mg/dl or lower and the glucose level decreases at a rate of from about 1 to about 2 mg/dl-min or higher, or the glucose level is about 70 mg/dl or lower.

17. A medical system comprising:
a monitoring device comprising an electronic control circuitry that is configured to monitor the rate of glucose level change in a subject, wherein said monitoring device further comprises a telemetry system;
a therapeutic substance delivery device comprising an electronic control circuitry that is configured to deliver insulin to the subject; and
a receiver-controller device comprising an electronic circuitry that is configured to receive a signal generated by said monitoring device and is further configured to control the operation of said therapeutic substance delivery device based on the rate of change in the selected state of the subject as monitored by said monitoring device wherein said receiver-controller is configured to reduce or stop administering insulin when the glucose level decreases and to automatically resume delivery of insulin according to the insulin sensitivity of the subject.

18. The medical system of claim 17, wherein said monitoring device monitors the rate of subcutaneous glucose level change.

19. The medical system of claim 17, wherein said receiver-controller is configured to reduce or stop administering insulin when the glucose level about 150 mg/dl or less and the glucose level decreases at a rate of about 2 mg/dl-min or higher.

20. The medical system of claim 17, wherein said receiver-controller is configured to reduce or stop administering insulin when the glucose level is about 70 mg/dl or lower.

* * * * *